United States Patent [19]

Seaman

[11] Patent Number: 4,651,556
[45] Date of Patent: Mar. 24, 1987

[54] MEASURING DEVICE

[75] Inventor: Donald J. Seaman, Oak Creek, Wis.

[73] Assignee: Seaman Nuclear Corporation, Milwaukee, Wis.

[21] Appl. No.: 652,493

[22] Filed: Sep. 18, 1984

Related U.S. Application Data

[63] Continuation of Ser. No. 305,155, Sep. 24, 1981.

[51] Int. Cl.[4] .................. G01N 9/24; G01N 19/10
[52] U.S. Cl. .................................. 73/32 R; 73/73
[58] Field of Search ............... 73/32 R, 73; 404/128, 404/131, 129; 378/50, 89; 250/491.1, 492.1

[56] References Cited

U.S. PATENT DOCUMENTS

| | | | |
|---|---|---|---|
| 1,676,941 | 7/1928 | Cantu | 404/131 |
| 2,172,313 | 9/1939 | Young | 33/DIG. 33 |
| 3,143,886 | 8/1964 | Lippke | 73/73 |
| 3,395,631 | 8/1968 | Smith | 250/492.1 |
| 3,628,375 | 12/1971 | Pagano | |

FOREIGN PATENT DOCUMENTS

| | | | |
|---|---|---|---|
| 1135762 | 5/1957 | France | 378/89 |
| 214508 | 4/1924 | United Kingdom | 404/131 |
| 598033 | 2/1948 | United Kingdom | 404/131 |

OTHER PUBLICATIONS

Brochure of "On Top", Roof Moisture Survey Service; Copyright 1979; Bulletin 1289 of Seaman Nuclear Corporation.

Density on the Run; Seaman Nuclear Corporation; no date but submitted as prior art brochure by applicant.

Primary Examiner—Charles Frankfort
Assistant Examiner—Denis E. Corr
Attorney, Agent, or Firm—Fred Wiviott

[57] ABSTRACT

A device for measuring density and moisture of a material includes a hollow roller rotatably mounted on a shaft for rolling movement on the surface of the material. A radioactive source and density and moisture detectors are supported below the shaft and adjacent to the inner surface of the roller at substantially a fixed distance from the surface of the material being measured as the roller is rolled. The detectors are coupled to a conventional counter and microprocessor circuitry which provide an output reading related to the density or moisture content of the material. The shaft may be mounted for tilting movement so that the roller may pitch in conformity to contours in the material surface.

22 Claims, 5 Drawing Figures

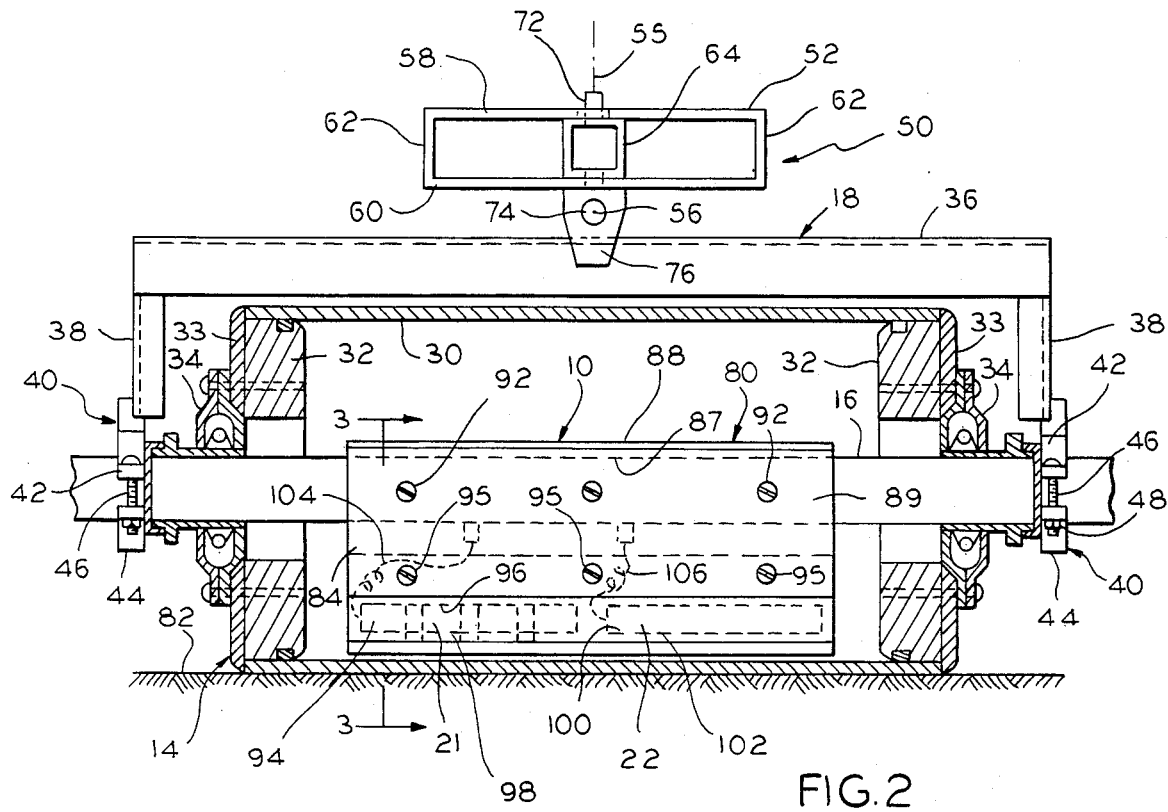

MEASURING DEVICE

This is a continuation of application Ser. No. 06/305,155, filed Sept. 24, 1981.

BACKGROUND OF THE INVENTION

This invention relates to measuring devices and more particularly a density measuring device which permits continuous operation as it traverses the surface of the material whose density is being measured.

In certain paving operations, such as, for example, when a layer of asphalt is applied to a pre-existing concrete roadway, the asphalt is commonly applied with a paver which lays the material at a preselected thickness. Typically, a roller is then employed for compacting the material. The actual density of the asphalt will be influenced by a number of factors, including the vibration frequency and amplitude of the compactor, ballast, the forward travel speed, the temperature of the material, the degree of overlap, the number of roller passes and roller travel speed, and the reaction surface to which the material is being applied. The thickness of the material being applied may also affect the efficiency of the compactor and therefor, influence density.

It is important to know the material density to prevent over-rolling. This occurs when the maximum density of the material has been attained and further compaction thereafter tends to loosen the material. Also, in the compaction of asphaltic concrete, it is important to know how close the compactor can approach the asphalt paver and how far behind it can traverse before chilling is encountered. If the compactor is too close to the paver, the hot material displaces and cannot be compacted. On the other hand, if the roller trails the compactor by too great a distance, the material will cool excessively at the far end of the traverse so that compaction in that area is also not possible.

It is, therefore, desirable to provide a method for rapidly and accurately determining the density of an applied layer while it was still hot so that corrections in the compacting operation can be made to eliminate the necessity for costly reworking.

SUMMARY OF THE INVENTION

It is an object of the invention to provide new and improved apparatus for measuring density.

A more specific object of the invention is to provide a density measuring apparatus which continuously measures the density of material as the apparatus traverses the material surface.

These and other objects and advantages of the invention will become more apparent from the detailed description thereof taken with the accompanying drawings.

In general terms, the invention comprises density measuring device having a hollow, rotatably mounted roller and a shielded radioactive source and a detector mounted within the roller and at a substantially fixed distance from the surface of the material whose density is being measured as the roller moves therealong. In the preferred embodiment the roller is universally mounted to permit the roller to conform to uneven surfaces.

BRIEF DESCRIPTION OF THE DRAWINGS

FIG. 2 is a side elevational view, partly in section, of the density measuring device according to the preferred embodiment of the invention;

FIG. 3 is a cross-sectional view taken along lines 3—3 of FIG. 2;

DESCRIPTION OF THE PREFERRED EMBODIMENT

Figure 1:
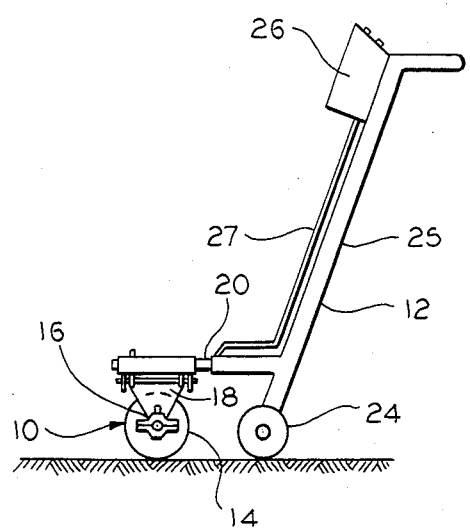
FIG. 1 shows one example of a mobile device in which the density measuring apparatus of the invention may be mounted.

FIG. 1 shows the measuring device 10 according to the preferred embodiment of the invention to be mounted on a manual transporter 12. In general terms, the measuring device includes a cylindrical roller 14 mounted for rotation on a shaft 16 which in turn is supported on a bracket assembly 18 carried adjacent the front end of the base 20 of transporter 12. A radiation source 21 and detectors 22 and 23 are supported within the roller 14 (see FIG. 5) as will be discussed more fully below. At the rear of the base 20 there are a pair of spaced apart wheels 24 and an upwardly extending frame 25' which terminates in 25. A microprocessor, a counter and a control panel 26 are mounted adjacent the upper end of frame 25' and are connected to the detectors 22 and 23 by conductors 27. It will be appreciated that the handle 25 and wheels 24 permit the assembly to be maneuvered and moved in any direction over the surface 82 of the material being measured. It will also be evident that by tipping the assembl back onto the wheels 24, the measuring device 10 may be transported independently of the roller 14.

The roller 14 is shown more specifically in FIGS. 2 and 3 to comprise a hollow, cylindrical member 30 and a pair of relatively thick annular end members 32 which are suitably secured to the cylindrical member 30 and provide a stiffening thereto. There are also an annular end cap 33 secured to each member and each supports a by suitable bearing 34 which rotatably support the roller 14 on the shaft 16. The shaft 16, the cylindrical member 30, the members 32 and the end caps 33 are preferably fabricated of the lightweight metallic material, such as aluminum. The surface of member 30 may also be coated with a material such as teflon so as to minimize the tendency of asphalt and other materials to adhere to its surface.

Figure 4:
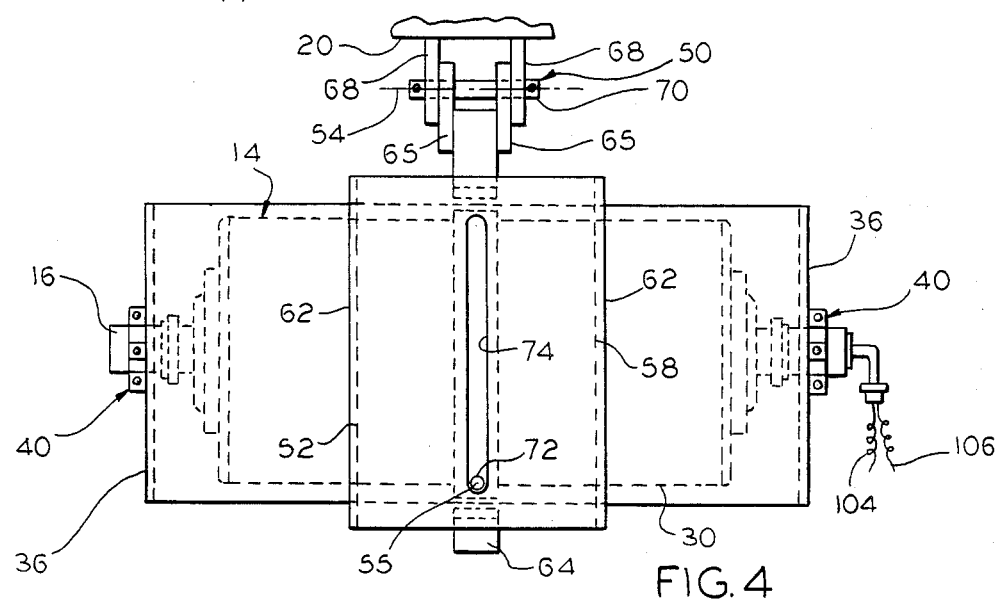
FIG. 4 is the top plan view of the density measuring device shown in FIG. 2.
Figure 5:
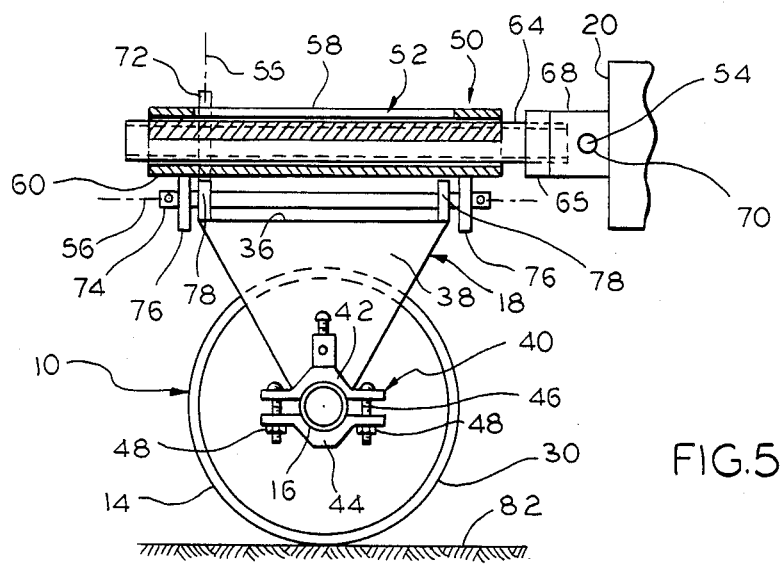
FIG. 5 is the side elevational view of the density measuring device shown in FIG. 2.

As seen in FIGS. 2, 4 and 5, the bracket 18 includes a generally rectangular top plate 36 and a pair of depending triangular side plates 38. A set of quick release clamps 40 secures the shaft 16 to the lower end of side plates 38 and in general parallels them with the top plate 36. In particular, each clamp 40 includes a top, downwardly facing jaw member 42 affixed to the lower corner of its associated side plate 38 and engaging the upper portion of shaft 16 and an upwardly facing lower jaw member 44 which engages the lower portion of shaft 16. The members 42 and 44 are interconnected by a pair of screws 46 which extend through suitable aligned openings formed in the ends of each clamp member and secured by nuts 48. The clamps 40 permit the rapid release of the shaft 16 from the bracket 18 so that the roller 14 and its radioactive source can be safely stored when not in use.

The bracket 18 is mounted on the base 20 by means of a universal support assembly 50 which permits the roller 14 to pivot three dimensionally so that it may follow the contour of the surface being traversed. More particularly, the assembly 50 includes a frame 52 which is connected to the base 20 for pivotal movement about a first axis 54 and which supports the bracket 38 for pivotal movement about second and third axes 55 and 56 lying in planes perpendicular to each other and to the first axis.

The frame 50 comprises a pair of parallel spaced-apart plates 58 and 60 which are interconnected by side portions 62. A hollow, rectangular rod 64 is disposed between plates 58 and 60 has a pair of appertured members 65 affixed to one end and disposed between a pair of spaced-apart appertured bracket members 68 mounted at the front of the carriage base 20. A pin 70 extends through the appertures in the members 65 and the bracket 68 and defines the first pivot axis 54. A second pin 72 extends upwardly from rod 64 at a point adjacent its opposite end and is received in a slot 74 formed in plate 58. The pin 72 defines the second pivot axis 55. Finally, a third pin 74 which defines the third pivot axis 56 extends through brackets 76 affixed in spaced-apart relation and extending downwardly from the plate 60. The pin 74 also extends through appertures formed-in-hinge members 78 affixed to the upper surface of plate 36.

Those skilled in the art will appreciate that the frame 52 and roller 14 supported thereby can pivot about the first axis 54 of pin 68 while the frame and roller can swivel on pin 72 relative to rod 64 and that the roller 14 can pivot about axis 56 of pin 74 or relative to frame 52. In this manner, the roller 14 is free to follow the contour of the surface of the material being traversed. In addition, the pin 72 and slot 74 permits the frame 50 and roller 14 to be repositioned relative to the base 20 to facilitate forward or rearward rolling movement relative to surface 82.

As seen in FIGS. 2 and 3, the source 21 and the detectors 22 and 23 are mounted on shaft 16 by means of a support assembly 80 such that the source and detectors will remain a relatively fixed distance above the surface 82 of the material being measured as the roller 14 is rolled therealong. More specifically, the assembly 80 includes a pair of elongated support members 84 and 86 which are generally L-shaped in vertical section and are respectively defined by short legs 87 and 88 and long legs 89 and 90. The member 84 is affixed to shaft 60 with its short leg 86 engaging the upper-most portion of shaft 16 and leg 89 extending downwardly along one side and in engagement therewith. In addition, member 86 is mounted with its short leg 88 engaging the leg 87 and its long leg 90 extending downwardly along the opposite sides of shaft 16. A plurality of screws 92 affix the members 84 and 86 to the shaft 60 so that the legs 89 and 90 extend vertically downwardly in a generally parallel, spaced relation. Disposed in the gap between the lower ends of legs 89 and 90 is an elongate, generally rectangular in section, shield 94 which is formed of any suitable material such as lead. The shield 94 is suitably secured in this position in any suitable manner, such as by screws 95. The source 21 is disposed in a first cavity 96 formed in shield 94. An opening 98 in the lower end of cavity 96 exposes the surface 82 immediately below the source 22 to the radiation emitting from source 21 while the shield 94 prevents radiation upwardly and to the sides. The first detector 23 is similarly disposed in a recess 100 in shield 92 and there is a similar opening 102 in the lower end of the shield which permits reflected or scattered radiation from the source 22 to impact the detector 22. Detector 23 on the other hand is positioned on the leg 90 exteriorly shield 92 and adjacent to the source 22. Electrical conductors 104 and 106 are connected to conductors 22 and 23 respectively and extend therefrom to the interior of shaft 16 from which they emerge at one end for connection to the counter, microprocessor and control panel 26.

It will be appreciated that as the roller 20 is rolled across the surface of the material being measured, the source 21 in the detectors 22 and 23 will remain in a relatively fixed distance above the surface 82 of the material. It will also be appreciated that because the assembly rests on rollers 20 and 24, the source and detector will remain in a perpendicular orientation relative to the surface 82 as the cart 12 is moved.

Those skilled in the art will appreciate that when a layer of asphalt, for example, is being applied to a base layer of another material, such as concrete, it is common to employ a device such as a paver, which is preset to apply material at predetermined thickness. To achieve the desired density, the asphaltic material must be compacted by making a number of passes over the asphalt layer with a heavy roller, for example. However, because of variables, such as temperature, ballasts, the surface to which the material is being applied, the frequency of vibration of the compactor and the number of roller passes, actual density of the material may vary. The deviation of any of these variables from optimums can substantially affect rolling times. The density measuring apparatus shown in accordance with a preferred embodiment of the invention can be used in conjunction with the roller to measure the material density as the roller is traversing its surface so that rapid adjustments can be made to insure compliance with specifications. In addition, adjustments in the variable factors can be made so as to minimize rolling times. Further, the device according to the invention permits the source 21 to be located relatively close to the surface 82 for safety and economy.

More specifically, the thickness of the top layer of asphalt material is first determined from the specifications, and that information is provided to the microprocessor 26. The microprocessor will also be provided with an instrument constant which is determined when the device is manufactured and which will depend upon the nature and strength of the source 21, the geometry of the apparatus and the sensitivity of the detectors 22 and 23 and will vary slightly from instrument to instrument.

Before the layer of material whose density is to be measured is applied, the density measuring device will be employed to provide an average density measurement for the sub-layer. This information will also be provided to the microprocessor for determination of density in a well-known manner. After the material laying apparatus has applied the surface layer and the same has been partially compacted by a roller, the manual transporter 12 will be passed over the surface and continuous reading of density will appear on the instrument panel 26 whereby the operator can immediately determine what further compacting or adjustments, if any, is required. Density is measured by the air-backscatter and will be calculated by the microprocessor in accordance with the method disclosed in U.S. patent application No. 227,913 filed Jan. 23, 1981 and assigned to the assignee of the present invention. In addition, moisture may be measured in the conventional manner by the detectr 23. For example, the method employed by the Seaman Nuclear Series 100 Density/Moisture Meter may be employed.

While only single embodiment of the invention has been illustrated and described, it is not intended to be limited thereby. For example, instead of mounting the roller 16 on a manual transporter, the same could be mounted directly on a roller compacter and with the microprocessor, counter and instrument panel mounted in position for easy observation by the operator. In this manner, the operator of the roller could make direct readings and adjust his rolling passes accordingly. Also, instead of employing a radioactive source other well known types of radiation sources, such as, X-ray tubes, microwave generators, electric-magnetic devices and the like, may be employed.

I claim:

1. A device for measuring density or moisture of a layer of material such as paving material,
   said device including moisture or density measuring means comprises a shielded radioactive source and a radiation detector, said source and detector being of a type wherein the radiation from the source which is received by said detector is a function of the density or moisture content of said material and their distance from the surface of the material being measured,
   transport means for moving said source and detector in any direction over the surface of said material,
   said transport means including a support, said detector and source being mounted on said support and oriented downwardly therefrom,
   a first roller mounted on said support for rotational movement thereon independant of said source and detector, said first roller having a cylindrical outer surface and a hollow space formed therein and surrounding the axis of rotation,
   meter means mounted on said transport means above said first roller to permit observation by an operator and coupled to said detector for providing an indication of the measured density or moisture,
   said source and detector being mounted on the support and disposed with the hollow space a predetermined distance from the surface of the first roller, the source and detector being directed toward the material,
   said first roller being of a relatively rigid material so that it will engage the surface of the material whose density or moisture is being measured with substantially line contact to maintain the detector and source a substantially constant distance above the surface of the material to minimize errors in the indication which otherwise results from variations in the distance of the source and detector from the surface whereby density or moisture measurements can be made of successive portions of the material on a continuous basis as the first roller is rolled across said surface,
   and second roller means mounted on said transport means and spaced from the first roller means for maintaining the orientation of said source and detector as said transporter is moved over the surface of said material.

2. The combination set forth in claim 1, and including a shaft fixed to said support means, said roller being rotatably mounted on said shaft, said source and detector being mounted on said shaft and in a fixed relation relative thereto.

3. The combination set forth in claim 2 and including a support extending downwardly from said shaft, shielding means mounted on said support, a first recess formed in said shielding means and having an opening in the lower end thereof, said source being disposed in said first recess whereby radiation from said source is directed downwardly and at a fixed distance above the line of contact between the roller and the surface of said material.

4. The combination set forth in claim 3 and including a second recess formed in said shielding means and spaced from said first recess, an opening formed in the lower end of said second recess, said detector being disposed in said second recess for receiving radiation upwardly through said opening.

5. The combination set forth in claim 3 wherein said detector is mounted on said support and exteriorly of said second recess but adjacent thereto.

6. The combination set forth in claims 3 and including mounting means for coupling said shaft to said support means, said mounting means being constructed and arranged to permit limited universal pivotal movement of said shaft relative to said transport means.

7. A device for measuring density or moisture including a transport means,
   a shaft,
   mounting means for coupling said shaft to said transport means,
   said mounting means including a frame,
   first means coupling said shaft to said frame for pivotal movement about a first axis,
   second means coupling said frame to said transport means for pivotal movement about a pair of axes which lie in planes perpendicular to each other and to a plane containing the first axis, said mounting means being constructed and arranged to permit limited universal pivotal movement of said shaft relative to said transport means,
   roller means rotatably mounted on said shaft,
   said roller means having a hollow space formed therein and around the axis of said shaft,
   a shielded radioactive source and radiation detector for measuring density or moisture and being mounted on said shaft and within said space,
   said source and detector being mounted on said shaft and a predetermined distance from the surface of said roller means whereby said roller means will engage the surface of the material whose density or moisture is being measured with substantially line contact to maintain said detector and sources substantially constant distance above the materials surface.

8. The combination set forth in claim 7 wherein said frame is coupled to said transport means for limited sliding movement in a direction generally parallel to said first axis.

9. The combination set forth in claim 7 and including means mounted on said frame support means and coupled to said detector for indicating the density of said material as said roller rolls over said surface.

10. The combination set forth in claim 8 and including support means extending downwardly from said shaft, shielding means mounted on said support means, a recess formed in said shielding means and having an opening in the lower end thereof, said source being disposed in said recess whereby radiation from said source is directed downwardly.

11. A density measuring device adapted to be mounted on a pavement roller-compactor for determining the density of the material being compacted, the improvement comprising:
   a support frame constructed and arranged to be coupled to said roller-compactor,
   roller means rotationally mounted on said support frame for rolling on said material as said roller compactor moves,
   said roller having a cavity formed therein and extending around its axis of rotation,
   a radiation source and a radiation detector for measuring density and mounted in said cavity on said frame a fixed distance from said axis of rotation and above the surface of said material along the line of contact between said roller and the material.

12. The combination set forth in claim 11 and including support means mounted on and extending downwardly from said support frame, said source and detector being mounted in spaced relation on said support frame and disposed adjacent the inner surface of said roller.

13. The combination set forth in claim 12 and including support means fixed to and extending downwardly from said support frame, said source and detector being mounted in spaced relation on said support means and disposed adjacent the inner surface of said roller.

14. The combination set forth in claims 12 or 13 and including means for mounting said support means to permit two directional tilting so that said roller can follow the contour of said material.

15. A device for measuring density or moisture including:
   a transporter,
   said device including support means mounted on said transporter,
   roller means mounted on said support means for rotational movement about an axis, said roller means having a hollow space therein and around said axis,
   a shielded radioactive source and a radiation detector for measuring density or moisture mounted on said support means and within said space, the radiation measured by said detector being directly related to the distance of the source and detector from the surface of the material being measured,
   said source and detector being mounted on said support means a predetermined distance from the surface of the first roller means,
   said roller means being formed of a relatively rigid material so that said first roller means will engage the surface of the material whose density or moisture is being measured with substantially line contact to maintain said detector and source a substantially constant distance above the material's surface and thereby minimize errors in measurements due to changes in contour the surface of the material being measured.

16. The combination set forth in claim 15 wherein said transporter comprises a cart.

17. The combination set forth in claim 16 and including a meter mounted on said transporter and connected to said detector for processing signals from said detector and for displaying an indication of density or moisture, said meter being mounted on said transporter in a position above the roller in which the source and detector are disposed to permit observation by an operator.

18. The combination set forth in claim 15 wherein said transporter comprises a roller compactor.

19. The combination set forth in claim 18 and including a meter mounted on said transporter and connected to said detector for processing signal from said detector and for displaying an indication of density or moisture, said meter being mounted on said transporter in a position above the roller member in which the source and detector are disposed to permit observation by an operator.

20. The combination set forth in claim 15 wherein said roller is formed of a nonfrangible material.

21. A measuring device for measuring the density or moisture of a material, the device having a shielded radioactive source and a radiation detector mounted on a first support, an enclosure mounted on the first support and surrounding the source and detector and having an arcuate outer surface for engaging the surface of the material whose density or moisture is being measured with line contact, the first support orienting the detector and source on the first support radially relative to the arcuate surface, said source and detector being mounted on said first support a predetermined distance from the arcuate surface, and a second support coupled to the first support and extending laterally thereof for engaging the surface of the material being measured at a location spaced laterally of the line of contact between the enclosure and the material for supporting the source and the detector in an orientation normal to the surface of the material and along the line of contact between the enclosure and the material surface.

22. The measuring device set forth in claim 21 wherein the enclosure comprises a hollow rotatably mounted roller, the first support comprising a transporter and the second support comprising a second roller for rolling the first roller over the surface without reorienting the source and detector.

* * * * *